United States Patent [19]

Kranz et al.

[11] 4,339,612
[45] Jul. 13, 1982

[54] PREPARATION OF 3,3-DIMETHYL-1-PHENOXY-BUTAN-2-OLS AS FUNGICIDE INTERMEDIATES

[75] Inventors: Eckart Kranz, Wuppertal; Peter Siegle, Cologne, both of Fed. Rep. of Germany

[73] Assignee: Bayer Aktiengesellschaft, Leverkusen, Fed. Rep. of Germany

[21] Appl. No.: 234,529

[22] Filed: Feb. 13, 1981

[30] Foreign Application Priority Data

Mar. 5, 1980 [DE] Fed. Rep. of Germany ....... 3008477

[51] Int. Cl.³ ........................................... C07C 43/205
[52] U.S. Cl. ................................. 568/649; 568/637; 568/638; 568/631; 568/643; 568/586; 568/587; 568/648; 260/465 F; 560/61; 548/262; 71/124
[58] Field of Search ............... 568/648, 649, 587, 643, 568/637, 638, 586, 631; 260/465 F; 560/61

[56] References Cited

U.S. PATENT DOCUMENTS 2,916,520 12/1959 Normant .......................... 568/648 X
3,912,752 10/1975 Meiser et al. ................... 424/269 X

OTHER PUBLICATIONS

Morrison et al., Organic Chemistry, 3rd Ed. (1973) 564,565,567.

*Primary Examiner*—Bernard Helfin
*Attorney, Agent, or Firm*—Sprung, Horn, Kramer & Woods

[57] ABSTRACT

3,3-Dimethyl-1-phenoxy-butan-2-ols of the formula

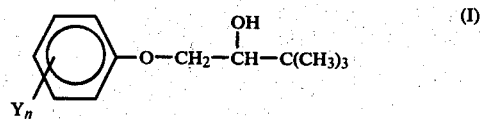

in which
Y is a halogen atom, an optionally substituted phenyl radical, an optionally substituted phenoxy radical or a nitro, cyano, alkyl, alkoxy, alkoxycarbonyl or cycloalkyl radical, and n is 0, 1, 2 or 3, exhibit plant growth stimulating properties and are also useful in the synthesis of known fungicides. They are produced from tert-butyloxirane and the corresponding phenols.

2 Claims, No Drawings

PREPARATION OF 3,3-DIMETHYL-1-PHENOXY-BUTAN-2-OLS AS FUNGICIDE INTERMEDIATES

The present invention relates to certain new 3,3-dimethyl-1-phenoxy-butan-2-ols, to a process for their production and to their use as intermediate products for the synthesis of known 1-azolyl-3,3-dimethyl-1-phenoxybutan-2-ones, which have fungicidal properties.

Several routes have already been disclosed for the preparation of the fungicidally active 1-azolyl-3,3-dimethyl-1-phenoxy-butan-2-ones (see for example, U.S. Pat. No. 3,912,752, issued Oct. 14, 1975; Ser. No. 885,053, filed Mar. 9, 1978 and the general statements in R. Wegler, "Chemie der Pflanzenschutz- und Schädlingsbekämpfungsmittel" (Chemistry of Plant Protection Agents and Agents for Combating Pests"), volume 4, page 208, Springer-Verlag, Berlin/Heidelberg/New York (1977). Because of the continual changes in the raw materials market, however, it seems necessary to look for new precursors and new process routes for the purpose of adapting better to the particular existing situation.

The present invention now provides, as new compounds the 3,3-dimethyl-1-phenoxy-butan-2-ols of the general formula

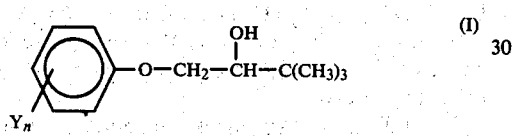

in which

Y represents a halogen atom, an optionally substituted phenyl radical, an optionally substituted phenoxy radical or a nitro, cyano, alkyl, alkoxy, alkoxycarbonyl or cycloalkyl radical and n is 0, 1, 2 or 3.

According to the present invention there is further provided a process for the production of a compound of the present invention characterized in that tert.-butyloxirane of the formula

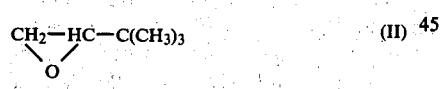

is reacted with a phenol of the general formula

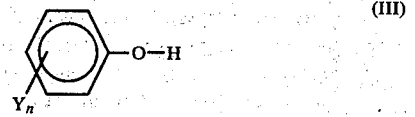

in which

Y and n have the abovementioned meanings, in the presence of a diluent and in the presence of a base.

The compounds according to the invention are interesting intermediate products for the preparation of known 1-azolyl-3,3-dimethyl-1-phenoxy-butan-2-ones, which have fungicidal properties.

The compounds according to the invention also exhibit growth-regulating properties.

Preferred compounds according to the present invention are those in which, Y represents a fluorine, chlorine, bromine or iodine atom, a phenyl or phenoxy radical which is optionally substituted by halogen (preferably chlorine), a nitro or cyano radical, a straight-chain or branched alkyl, alkoxy or alkoxycarbonyl radical with in each case 1 to 4 carbon atoms in the alkyl part, or a cycloalkyl radical with 5 or 6 carbon atoms, and n is 0, 1, 2 or 3.

The compounds of the following table may be mentioned as examples:

TABLE 1

$$\text{Ar}-O-CH_2-CH(OH)-C(CH_3)_3 \quad (I)$$

| $Y_n$ | $Y_n$ |
|---|---|
| 4-Cl | — |
| 4-F | |
| | 2-C$_6$H$_5$ |
| | 4-C(CH$_3$)$_3$ |
| 4-C$_6$H$_5$ | |
| 4-Br | 2,6-Cl$_2$ |
| 4-NO$_2$ | |
| 2,4-Cl$_2$ | 2,5-Cl$_2$ |
| 3-Cl | |
| | 2-Cl, 6-C$_6$H$_5$ |
| 4-Br, 2-Cl | 2-CH$_3$, 5-NO$_2$ |
| 2-OCH$_3$ | |
| | 4-I |
| 2,4-(CH$_3$)$_2$ | |
| 3,4-Cl$_2$ | 2-CH$_3$, 4-Cl |
| 3-Cl, 4-NO$_2$ | 2-F |
| 2-CH$_3$, 5-NO$_2$ | |
| | 2-CH$_3$ |
| 2-Br, 4-C$_6$H$_5$ | |
| | 3-Br |
| 4-C$_6$H$_5$ | |
| | 2-NO$_2$ |
| 2-C$_6$H$_5$ | |
| | 4-Cl, 3,5-(CH$_3$)$_2$ |
| 4-O-C$_6$H$_5$ | |
| | 4-CO-O-CH$_3$ |
| 2,6-Cl$_2$, 4-C$_6$H$_5$ | |
| | 4-C$_6$H$_4$-Cl |
| 2,4,6-Cl$_3$ | |
| | 2,6-Cl$_2$, 4-C$_6$H$_4$-Br |
| 2-Cl, 4-C$_6$H$_5$ | |
| | 2-Cl, 4-C$_6$H$_4$-Cl |
| | 4-O-C$_6$H$_4$-Cl |

If, for example, tert.-butyloxirane and 4-chlorophenol are used as starting substances, the course of the reaction for the production of compounds of the present invention is illustrated by the following equation:

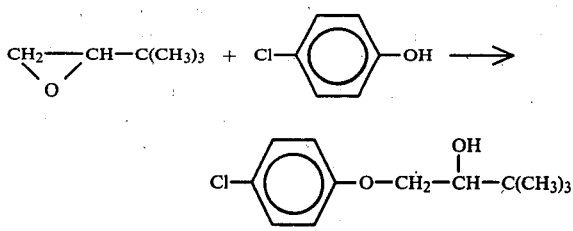

The tert.-butyloxirane of the formula (II) to be used as the starting substance in carrying out the process according to the invention is known (see for example, J. Chem. Soc. 1963, 1,321).

Preferred phenols of formula (III) also to be used as starting substances are those in which Y and the index n have the meanings which have already been mentioned in the description of the preferred compounds of the formula (I) according to the invention.

The phenols of the formula (III) are generally known compounds of organic chemistry.

The reaction according to the invention is carried out in the presence of a base. Bases which can be used are any of the customary organic and inorganic bases. These include, for example, amines (such as triethylamine), alkali metal hydroxides (such as sodium hydroxide and potassium hydroxide) and alcoholates (such as sodium methylate or ethylate and potassium methylate or ethylate).

Possible diluents for the reaction according to the invention are water and/or organic solvents. Examples which may be mentioned are: ketones (such as acetone and methyl isobutyl ketone), alcohols (such as methanol and ethanol), ethers (such as diisopropyl ether, tetrahydrofuran and dioxane), aromatic hydrocarbons (such as benzene and toluene) or formamides (such as dimethyl formamide).

The reaction temperatures can be varied within a substantial range in carrying out the process according to the invention. In general, the reaction is carried out between 0° and 150° C., preferably between 20° and 100° C.

In carrying out the process according to the invention, generally 1 to 2 moles, in particular 1 to 1.5 moles, of phenol of the formula (III) are preferably employed per mole of tert.-butyloxirane of the formula (II). The end products of the formula (I) are isolated in a generally customary manner.

As already mentioned, the new 3,3-dimethyl-1-phenoxy-butan-2-ols of the formula (I) are interesting intermediate products. They can easily be converted into 3,3-dimethyl-1-phenoxy-butan-2-ones of the formula

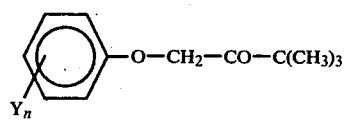

(IV)

in which

Y and n have the abovementioned meaning, by oxidation in the customary manner, for example with atmospheric oxygen, potassium permanganate, manganese dioxide, chlorine or potassium dichromate (see also the Preparative Examples); or by dehydrogenation in the customary manner, for example with noble metal catalysts, copper chromite or nitrobenzene.

The compounds of the formula (IV) can be converted into the corresponding 1-chloro (bromo)-3,3-dimethyl-1-phenoxy-butan-2-ones by further halogenation, preferably with sulphuryl chloride or with bromine, in the generally customary manner (see also DE-OS (German Published Specification) No. 2,401,715), and these products can be smoothly reacted with 1,2,4-triazole or imidazole to give the 1-azolyl-3,3-dimethyl-1-phenoxy-butan-2-ones of the formula

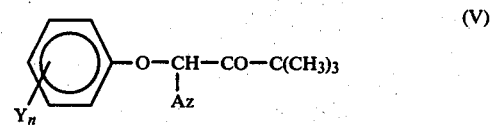

(V)

in which

Y and n have the abovementioned meaning and

Az represents 1,2,4-triazol-1-yl, 1,2,4-triazol-4-yl or imidazol-1-yl, (see also our DE-OS (German Published Specification) 2,401,715).

The 1-azolyl-3,3-dimethyl-1-phenoxy-butan-2-ones of the formula (V) having powerful fungicidal properties (see U.S. Pat. No. 3,912,752 issued Oct. 14, 1975 and U.S. Pat. No. 3,898,341 issued Aug. 5, 1975.

As also already mentioned, the new 3,3-dimethyl-1-phenoxy-butan-2-ols furthermore have a growth-regulating action.

The following comparison experiment shows, for example, the action of 1-(4-chlorophenoxy)-3,3-dimethyl-butan-2-ol in sugar-beet in comparison with the untreated control.

EXAMPLE 1

Influence on Growth of Sugar Beet

Solvent: 30 parts by weight of dimethylformamide
Emulsifier: 1 part by weight of polyoxyethylene sorbitane monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparations of active compound until dripping wet. After 14 days, the additional growth of the plants was measured and the influence on growth in percent of the additional growth of the control plants was calculated. 0% influence on growth denoted a growth which corresponded to that of the control plants. Negative values characterized an inhibition of growth in comparison to the control plants, while positive values characterized a promotion of growth in comparison to the control plants.

TABLE 2

| Influence on growth of sugar-beet | | |
|---|---|---|
| Active compound | Concentration in ppm | Influence on growth, in % |
| Control | — | −0 |

TABLE 2-continued

Influence on growth of sugar-beet

| Active compound | Concentration in ppm | Influence on growth, in % |
|---|---|---|
| 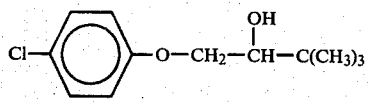 | 500 | +15* |

*Particularly thick leaves

PREPARATIVE EXAMPLE

EXAMPLE 2

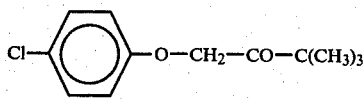 (a)

5 g (0.05 mole) of tert.-butyloxirane were added to 12.8 g (0.1 mole) of 4-chlorophenol and 4 g of sodium hydroxide in 20 ml of water. The reaction mixture was stirred at 60° C. for 24 hours and then diluted with about 100 ml of water. It was extracted three times with 50 ml of methylene chloride each time. The combined organic phases were washed with dilute aqueous sodium hydroxide solution for the purpose of removing unreacted phenol, and were dried over sodium sulpnate and concentrated. The residue was distilled in vacuo. 5.9 g (52% of theory) of 1-(4-chlorophenoxy)-3,3-dimethyl-butan-2-ol of boiling point 105° C./0.5 mm Hg were obtained.

Other compounds of Table 1 can be produced similarly.

SECONDARY PRODUCTS

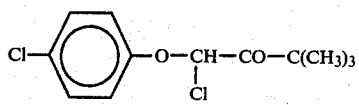 (b)

11.4 g (0.05 mole) of 1-(4-chlorophenoxy)-3,3-dimethyl-butan-2-ol were added to a mixture of 14.7 g (0.05 mole) of potassium dichromate in 12.25 g of sulphuric acid and 73.5 g of water at 30° C., whereupon the temperature rose to about 45° C. The mixture was stirred overnight at room temperature and then extracted three times with ether. The combined organic phases were washed with sodium bicarbonate and water, dried over sodium sulphate and concentrated. 7.8 g (69% of theory) of 1-(4-chlorophenoxy)-3,3-dimethyl-butan-2-one of melting point 58° C. were obtained.

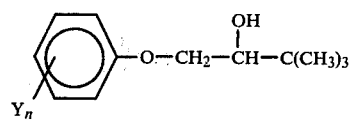 (c)

22.7 g (0.1 mole) of 1-(4-chlorophenoxy)-3,3-dimethyl-butan-2-one in 100 ml of carbon tetrachloride were warmed to 60° C. 16.2 g (0.12 mole) of sulphuryl chloride were added dropwise to this solution, without further warming, at a rate such that continuous evolution of gas took place. When the addition had ended, the mixture was stirred under reflux and was then concentrated by distilling off the solvent in vacuo. 1-(4-Chlorophenoxy)-1-chloro-3,3-dimethyl-butan-2-one was obtained in quantitative yield and was subsequently reacted directly, without further purification.

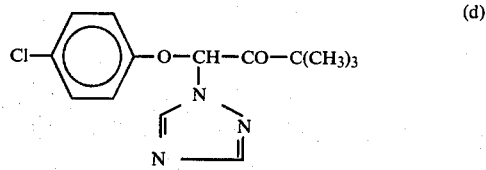 (d)

41.8 g (0.66 mole) of 1,2,4-triazole were dissolved in 300 ml of acetone. 93.4 g (0.72 mole) of anhydrous potassium carbonate were added to this solution, the suspension was heated to the boiling point and a solution of 156.5 g (0.6 mole) of 1-(4-chlorophenoxy)-1-chloro-3,3-dimethyl-butan-2-one in 150 ml of acetone was added dropwise at a rate such that the mixture boiled under reflux, without being heated. When the addition had ended, the mixture was heated under reflux for 15 hours in order to bring the reaction to completion; the resulting precipitate was then filtered off, washed with acetone and discarded. The filtrate was freed from solvent under a waterpump vacuum, the residue was taken up in 300 ml of toluene and the mixture was washed once with a solution of 10 g of 37% strength hydrochloric acid in 200 ml of water. The aqueous phase was separated off and discarded; the organic phase was washed with 500 ml of water and—after adding a further 400 ml of toluene—was stirred with a solution of 14.5 g of sodium hydroxide in 350 ml of water at room temperature for 6 hours. The organic phase was then separated off, washed with water until neutral and freed from solvent under a waterpump vacuum. 153.5 g (87% of theory) of 1-(4-chlorophenoxy)-3,3-dimethyl-1-(1,2,4-triazol-1-yl)-butan-2-one of melting point 75°-76° C. were obtained.

The compound and its fungicidal action are known (see U.S. Patent Specification 3,912,752).

It will be appreciated that the instant specification and examples are set forth by way of illustration and not limitation, and that various modifications and changes may be made without departing from the spirit and scope of the present invention.

What is claimed is:

1. A 3,3-dimethyl-1-phenoxy-butan-2-ol of the formula

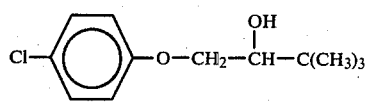

in which
Y is a fluorine, chlorine, bromine or iodine atom, a phenyl or phenoxy radical which is optionally substituted by halogen, a nitro or cyano radical, an alkyl, alkoxy or alkoxycarbonyl radical with in each case 1 to 4 carbon atoms in the alkyl moiety, or a cycloalkyl radical with 5 or 6 carbon atoms, and
n is 0, 1, 2 or 3.

2. A compound according to claim 1, wherein such compound is 1-(4-chlorophenoxy)-3,3-dimethyl-butan-2-ol of the formula

* * * * *